United States Patent [19]

Sengupta

[11] Patent Number: 4,966,962
[45] Date of Patent: Oct. 30, 1990

[54] REVERSE ANALOGUE OF ACTINOMYCIN D

[75] Inventor: Sisir Sengupta, Needham, Mass.

[73] Assignee: Trustees of Boston University, Boston, Mass.

[21] Appl. No.: 256,025

[22] Filed: Oct. 11, 1988

[51] Int. Cl.$^5$ .............................................. C07K 5/12
[52] U.S. Cl. .................................................. 530/317
[58] Field of Search .......................................... 530/317

[56] References Cited

U.S. PATENT DOCUMENTS 4,680,382 7/1987 Sengupta .............................. 530/317

Primary Examiner—James H. Reamer
Attorney, Agent, or Firm—Paul J. Cook

[57] ABSTRACT

A reverse analogue of actinomycin D (RAD) is provided which is effective in the therapeutic treatment of cancer. The analogue has the formula:

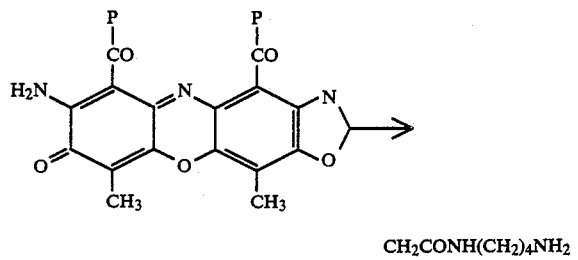

$CH_2CONH(CH_2)_4NH_2$ wherein P=

—Thr—D—Val—Pro—Sar—meVal=ppl (pentapeptidolactone).
|_____O_____|

1 Claim, No Drawings

REVERSE ANALOGUE OF ACTINOMYCIN D

BACKGROUND OF THE INVENTION

This invention relates to a new analogue of actinomucin D and to a method of preparing it.

Actinomycin D (AMD) is disclosed in German patent No. 1,172,680 and is a chromopeptide antibiotic whose potent activity in several tumors, including Wilm's tumor, gestaional choriocarcinoma and Kaposi's sarcoma, has been reported. It has the formula:

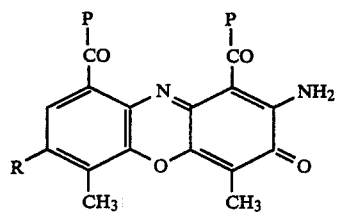

wherein P is the

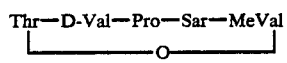

and R is hydrogen. AMD at submicromolar concentrations strongly inhibits DNA-dependent RNA synthesis and, to a lesser extent, DNA synthesis. Its interaction with DNA has been extensively studied, and the details of the mechanism of binding to DNA has been proposed, E. Reich, Cancer Res., 23,1428 (1963), W. Muller and D. M. Crothers, J. Mol. Biol., 35,251 (1968), and H. M. Sobell and S. C. Jain, J. MOL. Biol., 68,21 (1972). It has been assumed that the cytoxicity of AMD is due to its inhibition of RNA polymerase following the intercalative binding to DNA. It is quite possible, however, that the distortions in helical DNA resulting from the strong noncovalent association with AMD may not be solely responsible for the observed biological effects. For example, Nakazawa et al., J. Org. Chem., 46, 1493 (1981) suggest that an intermediate free-radical form of AMD may be the active form that causes DNA damage and cell death.

Furthermore, the proximal mechanism of biochemical action of AMD, which is evident from the inhibition of RNA synthesis, may not be the principal mechanism of selective cytoxicity of the agent at the pharmacological level. It is known that AMD is far more cytotoxic in those proliferating cells in which it inhibits DNA synthesis than in those of liver, kidney, muscle, etc., that are nonproliferating but are heavily dependent upon RNA synthesis for protein renewal.

Another pharmacological behavior of AMD is that it is not metabolized in vivo. Absence of metabolic conversion or detoxification of AMD leads to its accumulation in the cell nuclei of the host organs and causes cumulative toxicity. This acute cumulative toxicity limits the wide clinical application of AMD.

Reverse analogues and a symetrical analogue of AMD are disclosed in U.S. Pat. No. 4,680,382.

Accordingly, it would be desirable to synthesize new pharmacologically active analogues of AMD having increased drug efficacy. To achieve this, it would be desirable to increase the drug potency, by enhancing drug activity in the tumor cells, decrease toxicity to the host and improve means for administering the drug.

SUMMARY OF THE INVENTION

In describing this invention, the following notation as relates to the products of this invention is shown by Formula I.

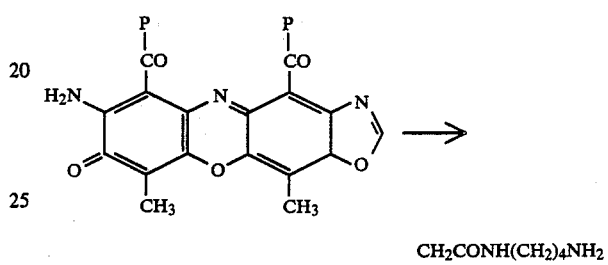

wherein
P=

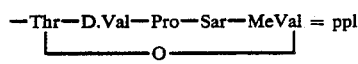

(pentapeptidolactone).

The compound is a novel compound and is active and toxic against human cancer cells.

The compound of this invention as well as closely related compounds to be tested for anticancer activity are produced by the schematic process as shown in Chart I.

DESCRIPTION OF SPECIFIC EMBODIMENTS

Two new classes of actinomycin D analogues are disclosed in U.S. Pat. No. 4,680,382. One class has tetracyclic chromophoric structure which features an oxazole ring attached to the phenoxazinone tricyclic ring of actinomycin D. This class is termed "reverse" analogues (RAD). The other class has the same tricyclic phenoxazinone ring of AMD, but carries two extra groups, an amino acid and a hydroxyl group. These moieties are substituted at the C-7 and C-8 positions. In this process, the unsymmetrical molecules of AMD is made symmetrical, and hence, it is termed a "symmetrical" analogue of SAD. (Chart I).

SCHEME I

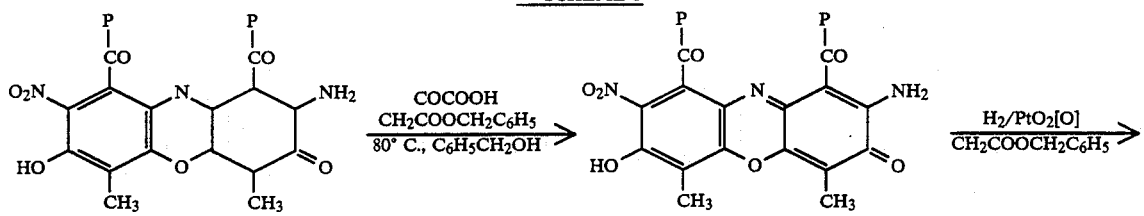

SCHEME I -continued

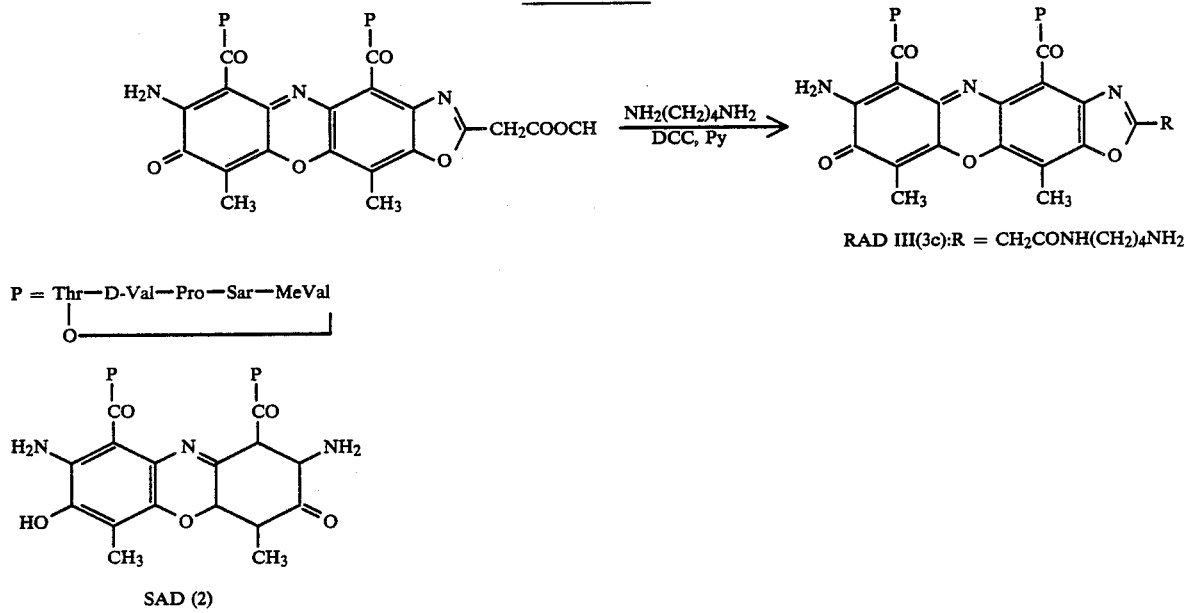

RAD III(3c):R = CH$_2$CONH(CH$_2$)$_4$NH$_2$

P = Thr—D-Val—Pro—Sar—MeVal

SAD (2)

RAD's usually carry a substitutent at the C-2 position; RAD I (3a) has a CH$_3$ substituent, and RAD II (3b) has a C$_6$H$_5$ substisubstituent. RAD I and RAD II and SAD (2) bind to double-stranded DNA strongly, but they do not intercalate. Yet they are potent inhibitors of nucleic acid synthesis and growth of tumor cells in vitro. RAD's also demonstrate strong antitumor activities agains P388 and L1210 leukemias and B$_{16}$ melanoma, and compared to AMD, they exhibit reduced toxicity in tumor-free hosts.

The tetracyclic RAD II is metabolized to tricyclic SAD, which is further metabolized to several biological conjugates including glucuronide and sulfate; these conjugates are several hundred times less cytoxic than SAD. In addition, the rat liver microsomes cause the conversion of RAD and SAD to their free-radical forms, which stimulate the production of superoxides. This process may contribute to their potent cytoxicity in tumor cells.

The new analogue of RAD, has a substituent chain, CONH(CH$_2$)NH$_2$, at the C-2 position on the oxazole ring of RAD. The substituent improves its aqueous solubility, which makes it easy to use for tumor experiments. The new analogue is RAD III (3c) (SchemeI).

The following example illustrates the present invention and is not intended to limit the same.

EXAMPLE

Synthesis of "Reverse" III AMD Analogue (RAD III, 3c). The synthesis of RAD III (3c) is shown schematically in Scheme I. Compound 4 was reacted with the benzyl ester of oxalacetic acid at 80° C. according to the procedure reported. The resulting product 5 with the CH$_2$COOCH$_2$C$_6$H$_5$ substituent at the C-2 of the oxazole ring was debenzylated to 6, and compound 6 was coupled with excess 1,4-diaminobutane by DCC in pyridine. The isolated product showed the characteristic UV-vis and NMR characteristics and the specific rotation values of a RAD compound with a CH$_2$CO(CH$_2$)$_4$NH$_2$ substituent. RAD III (3c) was polar and more soluble in water than either RAD I (3a), RAD II (3b), or actinomycin D(1) (solubility for RAD III is 2.1 mg/mL at 20° C. for AMD, 1.0 mg/mL at 20° C.). Like AMD and its other "reverse" analogues, RAD III (3c) is 16-fold more soluble in water at 4° C. than at 20° C.

RAD I (3a), RAD II (3b), and SAD (2). Like its predecessors RAD III shows UV-vis double-absorption peaks at 455 and 440 nm in chloroform, characteristic of a phenoxazin chromophore with o-aminoquinone substituents. The NMR chemical shifts of the chromophoric and peptide moieties are consistent with that found for the other RAD's. The specific rotation and the NMR values confirm that the peptide conformation in RAD III is practically the same as in AMD.

BIOPHYSICAL PROPERTIES

The equilibrium binding constants of RAD III (3c), determined from the Scatchard plots of binding isotherms with use of calf thymus DNA, are K$_{app}$, 2.9×10$^6$M$^{-1}$, and B$_{app}$, 0.040 in 0.01M phosphate buffer, pH 7.0 at 20° C. AMD (1) shows K$_{app}$, 2.3×10$^7$ M$^{-1}$, and B$_{app}$, 0.108;[2,7] K$_{app}$ of AMD is 1 log unit higher than RAD III, suggesting a weaker DNA binding for RAD III. In contrast to AMD, RAD III failed to demonstrate any measurable change in the intrinsic viscosity with the increasing ratios of [ligand]/[DNA base pair] in a viscometry experiment using low molecular weight DNA (0.5×10$^5$ to 1.0×10$^5$ daltons) The experiments showed that RAD III does not intercalate into DNA.

BIOCHEMICAL PHARMACOLOGY

It has been reported that the quinone imino chromophore of actinomycin can be subjected to enzyme-catalyzed single-electron reduction to give free-radical species that generate superoxides by reacting with molecular oxygen. The process needs a reductive cofactor NADPH, which is oxidized to NADP+ during the process, giving a change in the absorbance at 340 nm that can be measured spectrophotometerically. Alternatively, the superoxides generated during the process may be allowed to react with epinephrine to produce adrenochrome, a chromophore with strong absorbance at 480 nm that can be measured spectrophotmetrically.

The superoxide formations were studied via NADPH oxidation catalyzed by AMD analogues in the presence of rat liver microsomes. The results of these assays demonstrated that RAD and SAD are extremely efficient agents in stimulating these reactions. The process of adrenochrome formation is inhibited by superoxide dismutase, confirming that superoxide is indeed generated in these systems.

DNA-CLEAVING ABILITY

The cleavage of DNA was followed by monitoring of the conversion of supercoiled closed-circular pBR322 DNA to open-circular DNA (analyzed by agarose gel electrophoresis and quantitated by staining with 0.5 ug/mL of ethidium bromide for 30 min and densitometry; (Table II). SAD and RAD show strong DNA-cleaving ability in the presence of sodium hydrosulfite and ferrous chloride. Presumably, sodium hydrosulfite acts as a reducing agent and regenerates Fe(II) from Fe(III) to produce a continuous source of the active metal ion. When the DNA-cleaving reaction with the analogues was performed at 20° C., the ratio of cleaved DNA (open circular form DNA versus closed circular DNA) was almost maximum within 1 h. The efficiency of this cleavage is comparable to that of the drug bleomycin (BLM). Cleavage of DNA by the analogues is aided by the actinomycin chromopeptide moiety, which acts as a site-specific binder to DNA, and is effected by the aminoquinone function which is chelated to the ferrous ion during the process, and this is the likely candidate which generates the radical species.

In general, the analogues demonstrate extremely efficient DNA cleaving ability which is approximately 70% as potent as that of BLM. In this respect, actinomycin is only about 30% as efficient as its synthetic analogues, RAD III (3c) and SAD (2) (Table II). Metabolic Studies, Metabolism in the Presence of Tumor Cell Homogenates and Rat Liver Microsomes. Details of these studies are reported in Table III. The cell homogenates (P388 cells were sonicated and were incubated at 37° C. with analogues for 16 h. Rat microsomes were harvested from phenobarbital-induced rats by standard procedure. Incubations were carried out for 6 h in the presence of a NADPH-generating system, i.e., glucose-6-phosphate dehydrogenase and glucose 6-phosphate. The metabolites and their water-soluble conjugates were isolated and identified with the use of tritiated analogues.

It was observed that the RAD analogues are metabolized to SAD (2) with the loss of oxazole ring. By use of both microsomal and tumor systems, the metabolic conversion of RAD III (3c) was found to generate several biological conjugates. In tumor cells, a larger fraction of SAD (2) (30–50%) remains unmetabolized. SAD is found to form glucuronide and sulfate conjugates only in tumor cells. Fractions of large molecular protein adducts are also isolated from SAD (2) and RAD III (3c) in both tumor cells and microsomes, suggesting that other active metabolite(s), e.g., radical species, might have been formed (Table III). Isolation of SAD from RAD analogues is a very important step, because SAD is found to be a potent and effective antitumor agent in several murine tumor systems (Tables V-XII).

IN VITRO INHIBITION OF TUMOR CELL GROWTH

The comparative cell growth inhibitory activity of RAD's and SAD are reported (data in Table IV, supplementary material). The cell lines used are human lymphoblastic leukemia (CCRF-CEM), murine lymphocytic leukemia (P388) and lymphoid leukemia (L1210), and mouse melanoma ($B_{16}$). Compared to AMD, the analogues RAD and SAD demonstrate uniformly superior activity in all the cell lines; the best activities are found to be against the solid melanoma line $B_{16}$. The analogues SAD and RAD III are two to fourfold more potent than AMD in this cell line. In general, the cytotoxic potencies of the analogues are in the order:

SAD=RAD III>RAD II=RAD I>AMD.

Furthermore, the activity of the analogues against a human colon carcinoma HT-29 cell line in culture was evaluated. After the cells were treated for 2 h with 0.01–10.0 uM of the drugs at 37° C., the cells were washed with ice-cold PBS (phosphate buffered saline), and the cell viability was assessed by soft agar cloning. Cells viability was expressed as the percentage of colonies from the drug-treated cells relative to control cells after correcting for the cloning efficiency, which ranged from 60% to 80%. The values of the drug concentration producing 90% reduction in cell viability extrapolated from the plot of concentration of drug versus ability of colony formation again establish SAD (2) as the most effective agent ($L.D._{90}$32 0.1 uM) followed closely by RAD II (3b) ($LD_{90}$=0.2 uM) and RAD III (3c) ($LD_{90}$ value at 5.0 uM concentration.

IN VITRO INHIBITION OF NUCLEIC ACID SYNTHESIS IN TUMOR CELLS

AMD is known to inhibit RNA synthesis more efficiently than DNA synthesis in P388 culture; compared to AMD, the analogue SAD shows a very high potency and superior activity in inhibiting DNA synthesis in P388 cells.

In addition to the P388 cells, this inhibitory activity in human carcinoma HT-29 grown in tissue culture has been also examined. The values of the drug concentration producing 50% inhibition of the incorporation of [$^3$H]-thymidine and [$^{14}$C] uridine into nucleic acid macromolecules are presented in Table V. These values are taken as estimates of the inhibition of DNA and RNA synthesis. Following 2-h exposure, SAD and RAD preferentially inhibit the synthesis of DNA; AMD inhibits RNA synthesis preferentially. Furthermore, the inhibitory activities of these analogues are three-to fivefold higher than AMD; the order of potency of the analogues for their inhibition of DNA synthesis is:

SAD (2)>RAD III (3c)>RAD II (3b)>>AMD (Table V).

ANTITUMOR ACTIVITY IN VIVO

The analogues were tested for their antitumor activities in P388 lymphocytic leukemia in male $BDF_1$ mice. In this system, in which AMD is known to be very effective, RAD II, RAD III, and SAD are found to be two-to threefold more effective with respect to %ILS and also in producing long-time survivors (Table VI).

The analogues were also tested against P388/ADR murine leukemia following the standard protocol (Table VI). This tumor line is known to be resistant to intercalating agents including actinomycin D and adriamycin; however, the tumor is highly sensitive to mitomycin C, which is believed to act via activation of its quinone chromophore to a free radical form. Again, RAD III and SAD show the highest levels of activity in these tumor lines, and it was observed that these analogues do not intercalate into DNA. The activities of these analogues were found to be fairly high over a broader dose range compared to AMD in this and also in the AMD-sensitive P388/S lines.

Following a standard protocol (Table VII), the analogues were tested in vivo in $B_{16}$ melanoma; again, compared to AMD, RAD and SAD were found to be superior agents.

The analogues were moderately active against ip inoculated L1210 leukemia when the drugs were administered, also ip on a multidose treatment schedule (Table VIII) supplementary material); increases in survival time of 71–100% were observed, but there were no 60-day survivors. The activities of the analogues were better than the activity demonstrated by AMD in this tumor line.

Both RAD III (3c) and SAD (2) displayed significant activity against colon tumor 26 implanted in $CDF_1$ mice. Drugs were administered in three doses over 9-day period and produced a 50–150% increase in %ILS (by SAD) over controls, and the survival rate increased 10–40% at 60 days; these activities are superior to that demonstrated by adriamycin, which is known to be effective in this tumor line.

In view of favorable activity agianst colon 26 carcinoma, further experiments using the active analogues were carried out on the advanced colon adenocarcinomas of mouse colon 38. The results obtained on the colon 38 tumor are shown in Table X. Administered every 4 days, three times, starting on day 1 after tumor implant, RAD III (3c) and SAD (2) are about 150% as active as AMD at either equivalent doses; also, their optimum dose activities are either equivalent or better than a highly active agent, adriamycin. The superiority of RAD III and SAD over AMD in inhibiting colon 38 carcinoma is evident from the data of both tumor weight inhibition and increases in survival time of the treated over nontreated mice and the larger number of long-term survivors produced by these analogues.

Tables XI and XII show the effectiveness of SAD (2) and RAD (3b and 3c) against CX-1 human colon adenocarcinoma heterotransplanted into athymic mice, with three iv treatments with drugs on a weekly schedule starting on the 15th day of tumor transplant. AMD and the analogues were tested at doses of 45 and 60 ug/kg. The tumor responded remarkably well to the treatment of RAD III at doses of 45 and 60 ug/kg. The tumor also responded fairly well to SAD treatment but at 60 ug/kg only. RAD II (3b) showed marginal but positive activity, and AMD and adriamycin were ineffective in this tumor at the doses tested.

The result of treatment of mammary MX-1 and lung LX-1 show that at the doses tested AMD and the analogues RAD III and SAD were practically ineffective. Only adriamycin showed some positive response at 60 mg/kg.

The most significant results of these investigations are findings that analogues RAD III (3c) and SAD (2) are active against murine leukemias P388/S and P388/ADR, $B_{16}$ melanoma, and especially murine and advanced carcinomas of the colon tumors C26 and C38. The data are in good agreement with the superiority of RAD III (3c) and SAD (2) against human colon adenocarcinomas transplanted in athymic mice. The good agreement between the results obtained in antitumor activity test, carried out in such different systems as in conventional mice transplanted with syngeneic tumors and in nude mice transplanted with human tumors, makes us confident about the reliability of the data and the prospects of a real benefit from these analogues in the treatment of a major cancer, e.g. colon carcinoma in humans.

The analogues were also tested in tumor-free male mice for their $LD_{10}$ values (Table XIV). The animals were given a broad range of doses (ip) on days 1, 5, and 9. The maximum tolerated doses of AMD and the analogues that caused death in only 10% of the tested animals in 21 days (i.e., $LD_{10}$) were recorded as MTD. The data in Table XIV show that the MTD values of all the analogues are 7–14-fold higher than corresponding dose value of AMD; however, the MED values are about half the MED value of AMD. On the basis of these values, the calculated therapeutic index values of SAD is 96, and those of RAD I, II, and III are 60, 67, and 70, respectively.

The above data indicate that RAD and SAD show significant reduction in their toxicity in vivo compared to their very high levels of cytoxicity in cells in vitro. This may derive from several processes, e.g., the microsomal activation in cells, i.e., conversion form RAD to SAD and/or to the other bioactive forms (free radicals, superoxides) necessary for activation, followed by deactivation by processes of bioconjugation to generate inactive forms in the organs of host. A detailed examination of their in vivo metabolism in liver, in tumors, and in the whole animal and the pharmacokinetic distribution of the drug and the active and inactive metabolites in animal organs and tissues is important for understanding the mechanism of action and the reasons for the high therapeutic index values in tumor-bearing host animals exhibited by the new analogue of actinomycin D.

Melting points were determined on a Thomas-Hoover melting point apparatus at a heating rate of 2° C./min. Thin-layer chromatography was performed on silica gel plates (Brinkmann Instrument, Inc.). Solvent systems were (A) EtOAc-acetone (4:1), (B) $CHCl_3$—MeOH (9:1), and (C) cifferri, the organic phase of the mixture EtOAc—MeOH—$H_2O$(20:1:20). High performance liquid chromatography was carried out on a Varian Model 5020 gradient liquid chromatograph equipped with a Varian reversed-phase $C_{18}$ column with the following solvent systems: I, $CH_3CN$-5 mM $NH_4OAc$ buffer, pH 6.4 (68:32 isocratic), flow rate 1.5 mL/min; II, 65–95% water-methanol gradient for 60 min, 1 mL/min; III, 10–90% $H_2O$-MeOH gradient for 120 min, 1 mL/min, with UV-vis, variable-and fixed-wavelength dual detectors at 254, 440, 470 and 520 nm. IR spectra were obtained on a Perkin-Elmer model 237 Infracord with KBr micropellets or in chloroform solution. UV-vis spectra were obtained on a Gilford 250 spectrophotometer. Specific rotation values were determined in chloroform solutions with a Cary 60 spectropolarimeter. NMR spectra were obtained in a JEOL FQ 90-MHz spectrometer equipped with Fourier transform. All elemental analyses were within ±0.4%. The -keto acid ester was purchased from Aldrich Chemical Co. [$^3$H]-labelled actinomycin D was purchased from Amersham. Other labeled compounds were from New England Nuclear. Actinomycin D (NSC 3053, lot 49399) was purchased from Calbiochem. Calf-thymus DNA, glucarase (bovine liver), superoxide dismutase (E.C. 1.15.1.1), mitomycin C, and bleomycin sulfate were purchased from Sigma Chemical Co. Sephacryl S-200 superfine gel was purchased from Pharmacia Fine Chemicals, Uppsala, Sweden. NADPH, 1-epinephrine, and plasmid DNA pBR322 were obtained from Boehringer Mannheim and from Calbiochem-Behring, San Diego, Calif.

SYNTHESIS OF ANALOGUE RAD III (3c).

Compound 4(200 mg, 0.15 mmol) in benzyl alcohol was allowed to react with 100 mg of benzyl ester of oxalacetic acid at 80° C. (Chart I) according to the procedure disclosed in J. J. Med. Chem., 28,620(1985) by S. K. Sengupta, C. Kelly, R. K. Sehgal. Benzyl alcohol was removed at 60° C. (4 mm), and the residue was purified on a TLC plate (system A) to yield compound 5, $R_f$ 0.88, and further crystallized from heptane-$CH_2Cl_2$(1:3) to a pure red solid (175 mg, 75% yield); $\lambda_{max}$ ($\epsilon \times 10^{-3}$, $CHCl_3$) 290 nm (10,00), 303 (10.20), 320 (7.70), 392 (7.70), and 498 (8.90); IR (KBr) 6.5 $\mu$m (nitro peak); NMR ($CDCl_3$) 8.4–8 6 (m, 2 H) and 7.75–7.70 (m, 5H) all for $C_6H_5$, 4.07 (d, 2H, $C_6H_5CH_2$), 7.03 (s, 1H, 8-OH), 3.07 (d, 2H, 2-$CH_2$), 2.20 (s, 3H, 9-$CH_3$), and 2.50 (s, 3H, 11-$CH_3$). Anal. ($C_{72}H_{93}N_{13}O_{21}.H_2O$) C, H, N. Compound 5 (150 mg, 0.10 mmol) in methanol (20 mL) was hydrogenated in the presence of $PtO_2$. The initial purple color of the solution was discharged, and as the resulting yellow solution was being filtered, the filtrate started turning deep yellow in air. After filtration and evaporation of methanol, the residue was chromatographed on Woelm alumina I. Washing the column with $CH_2Cl_2$ and eluting with methanol gave a pure red solid (125 mg of 6, 90%): $\lambda_{max}$ ($CHCl_3, \epsilon \times 10^{-3}$), 247 nm (12.1), 435(12.9), and 450 (14.0); NMR ($CDCl_3$) $\delta$5.49 (d, 2H, 7-$NH_2$) no peak for $C_6H_5CH_2$ (at 7.70–8.40) or at 11.45 for 8-OH; $R_f$ 0.35 (system A), Anal. ($C_{65}H_{87}N_{13}O_{19}.H_2O$) C, H, N.

Compound 6 (100 mg, 0.07 mmol) was dissolved in dry pyridine (3 mL) at 60° C., and 50 mg of dicyclohexylcarbodimine (DCC) was added followed by 15 mg of 1, 4-diaminobutane, $H_2N(CH_2)_4NH_2$(DAB): the mixture was stirred at 60° C. for 5 h. Excess DCC was decomposed with ice-cold $H_2O$, the precipitated dicyclohexylurea was filtered, and unreacted DAB and pyridine were removed at 60° C. (4 mm). The residue was dissolved in 1.0N HCl and extracted in $CH_2Cl_2$, and acidic layer was lyophilized.

The product, RAD III (3c), crystallized from THF gave a red solid (85 mg, 80%); Rf 0.51 (system A); $\lambda_{max}$ ($CHCl_3$, $\epsilon \times 10^{-3}$) 249 nm (15.1), 440 (14.1), and 455 (15.7); IR(KBr), no COOH peak; NMR ($CDCl_3$) $\delta$6.3 (m, 2H,$\omega$-$NH_2$), 5.45 (d, 2H, 7-$NH_2$), 3.77 (d, 2 H, 2-$CH_2$), 3.90–3.00 (m, 8H, $(CH_2)_4$), 2.81 (s, 3H, 11-$CH_3$), and 2.66 (s, 3H, 9-$CH_3$); $[]^{20}$ $-288\pm18°$ C. (c 0.1, $CHCl_3$;HPLC $t_R$ 3.9 min (system I) and 17.9 min (system II). Anal. ($C_{66}H_{97}N_{15}O_{18}.2H_2O$) C, H, N.

REACTION OF pBR322 with SAD and with BLM

Plasmid DNA pBR322 (0.5 ug) was dissolved in /8 $\mu$L of a reaction buffer (5 mM $Na_2SO_4$, 10 mM Tris-HCl). To this solution, 1 $\mu$L of the 10 mM aqueous solution of the agent containing 1 mM $FeCl_2$ was added. The mixture was incubated for 0.5–2 h at 20° or 37° C. Then, the incubation mixture was mixed with 10 uL of sample loading buffer (50% glycerin in 2 X Boyer's buffer containing 0.01% bromophenol blue). Finally, 5 uL of the mixture was analyzed by 0.7% agarose gel electrophoresis (120 V, Boyer's buffer; the migration distance of bromophenol blue was 5.0 cm). The gel was stained with 0.5 ug/L of ethidium bromide and then quantitated by densitometry.

INHIBITION OF NUCLEIC ACID SYNTHESIS IN TUMOR CELLS IN VITRO

DNA and RNA synthesis in P388 and HT-29 cells lines was monitored in the presence of drugs, and the rates of inhibition of their synthesis were estimated from the amounts of [2-$^{14}$C]-uridine and [$^3$H]-thymidine into RNA and DNA, respectively, according to the methods described previously.

In brief, for HT-29 colon carcinoma monolayer cells, $10^4$ cells in each of five wells per concentration, were incubated with radiolabelec nucleosides (0.5 Ci each) for the last hour of a 2-h drug exposure, following which the cells were aspirated and washed with buffered medium. Cells were trypsinized and counted in the Coulter counter. The cell suspensions were then precipitated onto glass fiber filter discs (Whatman 934H), with 10% trichloracetic acid and twice with 95% ethanol and dried, and the incorporation of radionucleotides was estimated.

In addition, to investigate the cross contamination of radioactivity from [2$^{14}$C] uridine, the cells were lysed with ice-cold 1% Triton X for 2.5 min. Macromolecules were precipitated with the addition of 10% perchloric acid (5% in the medium) and centrifuged; the pellet in 1% NaCl was treated with an equal volume of phenol reagent, the emulsion was centrifuged at 10000 g for 30 min at 4° C., and the separated layer was adjusted to 1% NaCl and treated with an equal volume of 2-ethoxyethanol to precipitate the nucleic acids. The precipitate was washed with 75% ethanol and dissolved in an aqueous solution containing 2% sodium acetate and 1.5% NaCl. An aliquot was used for estimation of the total radionucleotide incorporation. Ribonuclease, previously heated to 80° C. for 10 min to destroy deoxyribonuclease activity, was added, and the mixture was incubated at 37° C. for 30 min. DNA was thus freed from RNA with the addition of 2-ethoxyethanol as in the above and was found to have minimal radioactivity (8–12% of the total incorporated); the supernatant, which contained all of the RNA digest, accounted for the remainder, 87–92%, of the radioactivity found in the above-mixture of nucleic acids, demonstrating only a marginal contamination in the DNA from the added [2-$^{14}$C] uridine.

TABLE 1

Stimulation of NADPH Oxidation and Adenochrome Formation by Actinomycin D and its Analogues by Rat Hepatic Microsomal Incubations.

| compd | NADPH oxidation[a] nmol/min per mg of protein | SOD[b] 5 ug/mL | adrenochrome formation[a] nmol/min per mg of protein |
|---|---|---|---|
| no drug | 9.11 ± 0.30 | — | 2.11 ± 0.11 |
| AMD(1) | 10.01 ± 0.90(9.9) | — | 2.29 ± 0.33(8.5) |
|  |  | + | inhibited |
| SAD(2) | 64.3 ± 2.11(606) | — | 19.3 ± 1.04(815) |
|  |  | + | inhibited |
| RAD II(3b) | 65.0 ± 5.95(610) | — | 18.8 ± 1.9(800) |
|  |  | + | inhibited |
| RAD III(3c) | 87.1 ± 7.1(812) | — | 22.1 ± 2.2(870) |

TABLE 1-continued

Stimulation of NADPH Oxidation and Adenochrome Formation by Actinomycin D and its Analogues by Rat Hepatic Microsomal Incubations.

| compd | NADPH oxidation[a] nmol/min per mg of protein | SOD[b] 5 ug/mL | adrenochrome formation[a] nmol/min per mg of protein |
|---|---|---|---|
| | | + | inhibited |

[a]The percentage stimulation = (drug-stimulated rate basal rate)/basal rate × 100 and is shown in parentheses. NADPH oxidation was measured at 340 nm and adrenochrome formation was measured at 489 nm; the values are average ± standard errors of triplicate analyses. [b]SOD, superoxide dismutase.

TABLE II

Percentage of Closed Circular pBR322 DNA Cleaved by BLM and AMD Analogues[a]

| compd | concn, M | %[b] |
|---|---|---|
| AMD(1) | 10 | 10 |
| | 100 | 22 |
| SAD(2) | 10 | 35 |
| | 25 | 50 |
| | 50 | 50 |
| | 100 | 65 |
| RAD III(3c) | 10 | 40 |
| | 25 | 45 |
| | 50 | 50 |
| | 100 | 58 |
| BLM (bleomycin) | 10 | 55 |
| | 50 | 75 |
| | 100 | 85 |

[a]Ten microliters of 200 μM pBR322 DNA nucelotides in UM 10 mM Tris-HCl (pH 7.8) and 50 mM NaCl, containing 4 mM $Na_2-S_2O_4$ and 100 μM $FeCl_2$, was incubated with drug concentration at 20° C. for 1 h; the reaction mixture was kept saturated with air throughout the incubation period.
[b]Percentage of DNA was calculated from the amounts of open-and closed-circular DNA in the incubation mixture.

TABLE III

Percent Metabolite Isolated from Incubation Mixture Containing Tumor Cell Homogenate (T) or Rat Microsomes (M)

| drugs examined | AMD(1), % | SAD(2) % | RAD III (3c), % |
|---|---|---|---|
| uncoverted | 100(T,M) | 30.0 ± 3.0(T), 50.0 ± 10.5(M) | 20.0 ± 2.5(T), 10.0 ± 1.0(M) |
| SAD, 7,7 min(I) | | | |
| 20.0 min(II)[a] | | | 20.0 ± 2.0(T), 65.0 ± 5.5(M) |
| | | 47.0 ± 6.5(T), nil(M) | |
| SAD-glucuronide and/or sulfate, 8.0, 10.5 min(II); 16.0, 21.0 min(III)[a] | | | 40.0 ± 5.5(T), nil(M) |
| | | 5.5 ± 1.5(T), 20.0 ± 5.0(M) | |
| protein conjugates | | 7.5 ± 1.0(T), 15.0 ± 3.0(M) | 8.0 ± 2.0(T), 10.0 ± 10(M) |
| tissue bound | | | 5.0 ± 1.0(T), 5.0 ± 0.5(M) |
| unidentified metabolite | | 10.0 ± 1.0(T), 15.0 ± 4.0(M) | 5.0 ± 2.0(T), 8.0 ± 1.0(M) |

[a]HPLCt$_R$ in minutes (systems used were I, II, and III).

TABLE V

Synthesis by AMD and Analogues in Tumor Cells in Vitro

| | IC$_{50}$ values nM | | | |
|---|---|---|---|---|
| | P388 | | HT-29[a] | |
| compd | DNA synth | RNA synth | DNA synth | RNA synth |
| SAD (2) | 12 ± 4 | 15 + 2 | 70 ± 11 | 55 ± 6 |
| RAD III (3c) | 430 ± 38 | 55 ± 7 | 365 ± 45 | 45 ± 8 |
| RAD II (3b) | 780 ± 66 | 70 ± 5 | 580 ± 55 | 68 ± 10 |
| AMD (1) | 1100 ± 90 | 50 ± 5 | 900 ± 80 | 100 ± 11 |

[a]Human colon carcinoma in culture, IC$_{50}$, drug concentration producing a 50% inhibition of incorporation of precursor [$^3$H] thymidine into DNA and [$^{14}$C] uridine into RNA in the cell lines, isolated as acid preciptable materials. Data are average of replicate experiments.

TABLE VI

Activity of Actinomycin D (AMD) and "Reverse" (RAD) and "Symmetrical" (SAD) Analogues in P388 in Vivo. AMD-Sensitive and Adriamycin-Resistant Leukemia[a]

| drug | dose range mg/kg per inj, ip | P388/S optimal dose mg/kg, % ILS | P388/ADR[b] optimal dose, mg/kg, % ILS |
|---|---|---|---|
| adriamycin | 2.5–4.5 | 3.0,97(1/8) | 3.5,33 |
| actinomycin D(AMD) | 0.075–2.5 | 0.25,132(1/8) | 0.25,22 |
| RAD II (3b) | 0.10–0.8 | 0.35,382(4/8) | 0.6,132(1/8) |
| RAD III (3c) | 0.10–1.0 | 1.0,386(6/8) | 1.0,188(2/8) |
| SAD (2) | 0.3–1.8 | 0.6,382(4/8) | 1.2,176(3/8) |
| mitomycin C | 1.0–5.0 | 3.0,136(1/8) | 3.0,400(5/8) |

[a]Male CDF$_1$ mic inoculated ip: 10$^6$ cells inoculum, day 0. Drugs administered in 10% dimethyl sulfoxide-saline on days 1, 5, and 9. % ILS = percent increase in life span. Fractions in parentheses = tumor free survivors/total on day 60[b]. P388/S (adriamycin sensitive) and P388/ADR (adriamycin resistant) tumors were evaluated in the same experiment with agent listed.

TABLE VII

In Vivo Antitumor Activity of AMD, RAD, and SAD against B$_{16}$ Melanoma[a] Treatment: Days 1, 5, 9

| compd | optimal dose μg/kg per inj | MST[b] (range) | % ILS (surv)[c] |
|---|---|---|---|
| no drug (control) | | 29(20–48) | |
| actinomycin D(AMD,l) | 250 | 43(36–54) | 48(2/9) |
| RAD I (3a) | 300 | 65(55–62) | 124(6/9) |
| RAD II (3b) | 300 | 59(53–59) | 103(5/9) |
| RAD III (3c) | 300 | 62(53–61) | 114(6/9) |
| SAD (2) | 300 | 57(33–61) | 96(4/9) |

[a]0.2 mL of 1:5 (weight/volume) brei of B$_{16}$ melanoma implanted ip on day 0 in groups of nine BDF$_1$ mice. Drugs administered ip[b]. MST (range), median survival time in days (range of days for death of individual animal). [c]% ILS (surv), percent increase in life span (survivors on day 65/total injected).

TABLE X

Activity of Actinomycin D and Its Analogues against Advanced Colon Carcinoma C38 Tumor in CDF$_1$ Mice[a].

| compd | dose mg/kg | %[b] inhibn of tumor | % T/C[c] | toxic deaths[d] |
|---|---|---|---|---|
| AMD(1) | 0.075 | 30 | 100 | 0/9 |
| | 0.15 | 30 | 107 | 1/9 |
| | 0.30 | 67 | 134 | 0/9 |
| | 0.45 | 83 | 170 | 1/9 |
| | 0.60 | 89 | 103 | 4/9 |
| adriamycin | 2.0 | 29 | 103 | 0/9 |
| | 3.0 | 70 | 98 | 0/9 |
| | 4.0 | 93 | 250(5/9) | 3/9 |
| | 5.0 | | | 8/9 |
| RAD II (3b) | 0.15 | 29 | 103(1/9) | 1/9 |
| | 0.30 | 70 | 137 | 0/9 |
| | 0.60 | 83 | 170(3/9) | 0/9 |
| | 1.20 | 88 | 103(2/9) | 4/9 |
| RAD III (3c) | 0.30 | 80 | 170(1/9) | 0/9 |
| | 0.60 | 93 | 250(6/9) | 4/9 |
| | 1.20 | 94 | 231(3/9) | 2/9 |
| SAD (2) | 0.30 | 95 | 278(5/9) | 0/9 |
| | 0.60 | 97 | 278(6/9) | 0/9 |
| | 1.20 | 99 | 211(2/9) | 4/9 |

[a]CDF$_1$ mice were injected sc with colon 38 adenocarcinoma fragments (70 mg) and treated with drugs with iv injections on day 1, 5, and 9 following tumor imoplantation on day 0. [b]{100- (tumor weight of treated mice/tumor weight of untreated mice)} × 100; data pooled from two experiments, tumors measured on day 21 after implantation [c](Median survival time of treated mice/median survival of untreated mice) × 100; in parenthesis, number of over 100-day survivors/number of mice in a group of nontumored mice treated in parallel with the tumor-bearing mice and observed for 100 days.

TABLE XI

Experimental Chemotherapy of Human Colon CX-1 Tumor Heterotransplanted in Nude Mice

| | | | | | | tumor regression[a] | | | | | | | |
|---|---|---|---|---|---|---|---|---|---|---|---|---|---|
| | adriamycin, mg/kg | | | | AMD(1), μg/kg | | | RAD II (3b)μg/kg | | RAD III (3c) μg/kg | | SAD(2)μg/kg | |
| expt | 4,4 | 6.0 | 6.6 | 10.0 | 30 | 45 | 60 | 45 | 60 | 45 | 60 | 45 | 60 |
| 1 | − | + | + | +[b] | ± | + | +[b] | + | ++[b] | +++[b] | +++[b] | +++[b] | +++[b] |
| 2 | − | + | ND | + | − | ± | + | ± | + | ++ | ++[b] | + | ++[b] |
| 3 | − | ± | + | + | ± | + | +[b] | + | ++ | +++[b] | ++++[b] | ++[b] | +++[b] |

[a]−, % T/C high than 50%; ±, % T/C close to 50%; +, % T/C from 50% to 35%; ++, % T/C from 35% to 20%; +++, % T/C lower than 20%; ++++, regression of the tumor to a volume lower than 10% of the volume at the start of treatment. [b]Statistically significant as evaluated by the Students t test. [c]ND not done.

TABLE XII

Activity of Actinomycin D and Its Analogues, RAD and SAD against Human Colon Carcinoma CX-1 Tumor Heterotransplanted in Nude Mice

| compd | dose[a] μg/kg | TST[b] | % T/C, optimal |
|---|---|---|---|
| adriamycin | 6 × 10³ | 15 | 38(22)[c] |
| | 10 × 10³ | 15 | 39(22) |
| AMD (1) | 45 | 15 | 34(22) |
| | 60 | 15 | 36(22) |
| RAD II (3b) | 45 | 15 | 48(22) |
| | 60 | 15 | 24(22) |
| RAD III (3c) | 45 | 15 | 5(22) |
| | 60 | 15 | 3(22) |
| | 75 | 18 | 13(27) |

TABLE XII-continued

Activity of Actinomycin D and Its Analogues, RAD and SAD against Human Colon Carcinoma CX-1 Tumor Heterotransplanted in Nude Mice

| compd | dose[a] μg/kg | TST[b] | % T/C, optimal |
|---|---|---|---|
| SAD (2) | 40 | 15 | 18(22) |
| | 55 | 15 | 19(22) |
| | 70 | 15 | 5(32) |

[a]Intravenous treatment, once a week for three weeks; eight mice per group. [b]TST; number of days between tumor transplant and starting of treatment. [c]Numbers in parentheses; day of observation after the start of treatment.

TABLE XIV

Comparison of AMD with Chromophore-Substituted and Tetracyclic Chromophoric Analogues of AMD vs P388 Leukemia[a]

| drug | MED[b] | MTD[c] | therapeutic index MTD/MED |
|---|---|---|---|
| AMD (1) | 0.0625 | 0.25 | 4 |
| RAD I(3a) | 0.03 | 1.80 | 60 |
| RAD II(3b) | 0.03 | 2.00 | 67 |
| RAD III(3c) | 0.05 | 3.50 | 70 |
| SAD (2) | 0.025 | 2.40 | 96 |

[a]Drugs administered ip once on days 1, 5, and 9 starting 1 day after tumor implantation. Determinations were made from analysis of plotted log-dose response data. [b]MED (minimum effective dose) is the dose (milligram/killogram) providing an increase in life span of 45% over control in P388 tumor bearing mice. [c]MTD (maximum tolerated dose) is the lethal dose (milligram/kilogram) for 10% normal BDF$_1$ male mice (18–22 g); animals observed for deaths during 21 days (LD$_{10}$ = 21 days). Values were calculated from a plot of log dose vs percent mortality.

I claim:

1. The compound having the formula:

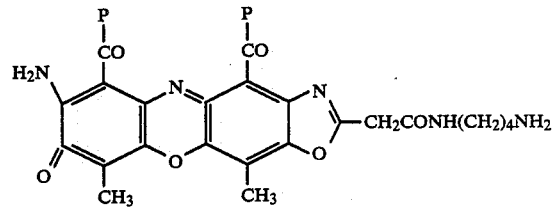

wherein P=

—Thr—D—Val—Pro—Sar—MeVal.
                    └————O————┘

* * * * *